(12) United States Patent
Hanafusa (10) Patent No.: US 8,097,470 B2
(45) Date of Patent: *Jan. 17, 2012

(54) MICROCHIP ANALYSIS METHOD AND APPARATUS

(75) Inventor: Nobuhiro Hanafusa, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 1022 days.

This patent is subject to a terminal disclaimer.

(21) Appl. No.: 11/488,037

(22) Filed: Jul. 18, 2006

(65) Prior Publication Data

US 2008/0017511 A1   Jan. 24, 2008

(51) Int. Cl.
    *G01N 1/38*   (2006.01)
(52) U.S. Cl. ......... 436/180; 204/451; 204/601; 422/502
(58) Field of Classification Search ............... 204/451, 204/601; 422/502–508; 436/174–180
    See application file for complete search history.

(56) References Cited

U.S. PATENT DOCUMENTS

| | | | | |
|---|---|---|---|---|
| 5,989,402 A * | 11/1999 | Chow et al. | ............... | 204/601 |
| 6,043,506 A * | 3/2000 | Heffelfinger et al. | ......... | 250/584 |
| 6,121,053 A * | 9/2000 | Kolber et al. | ............... | 436/172 |
| 7,033,475 B2 | 4/2006 | Nakamura et al. | | |
| 2004/0007675 A1* | 1/2004 | Gillispie et al. | .......... | 250/458.1 |
| 2005/0161402 A1 | 7/2005 | Hanafusa et al. | | |

FOREIGN PATENT DOCUMENTS

| | | | |
|---|---|---|---|
| JP | H10-148628 A * | 6/1998 | |
| JP | 10-246721 | 9/1998 | |
| JP | 2002-131279 A | 5/2002 | |
| JP | 2002-131280 A | 5/2002 | |
| JP | 2005-214710 | 8/2005 | |

OTHER PUBLICATIONS

N. Kondo; "Microchip technology no jitsuyoka," Bunseki, No. 5; 2002; 267-270./ English abstract is attached./ Discussed in the specification.

M. Liu et al.; "DNA fragment analysis by an affordable multiple-channel capillary electrophoresis system," Electrophoresis 24: 2003; pp. 93-95. / Discussed in the specification.

B. He et al.; "Fabrication of nanocolumns for Liquid Chromatography," Anal. Chem. 70; 1998; pp. 3790-3797./ Discussed in the specificaiton.

Office Action mailed Aug. 18, 2009, issued on the Japanese Patent Application No. 2004-135090 and English translation thereof.

* cited by examiner

*Primary Examiner* — Jeffrey T Barton
*Assistant Examiner* — J. Christopher Ball
(74) *Attorney, Agent, or Firm* — Edwards Wildman Palmer LLP (57) ABSTRACT

The analysis apparatus for microchips, each at least having a main flow path performing migration of a sample for analysis inside a sheet-like member, comprises a holding part holding microchips so that the multiple main flow paths are provided; a pretreatment part common to the multiple main flow paths for performing a pretreatment step prior to an analysis step in each of the multiple main flow paths; a processing part for performing analysis in each of the main flow paths independently of the others; and a control part controlling an operation in the pretreatment part so that when a pretreatment step for one main flow path ends, a pretreatment for a next main flow path starts and further controlling an operation in the processing part so that an analysis is subsequently performed for the main flow path where the pretreatment step has ended.

11 Claims, 7 Drawing Sheets

MICROCHIP ANALYSIS METHOD AND APPARATUS

FIELD OF THE INVENTION

This invention relates to a microchip analysis method and an apparatus thereof performing analysis of those such as a microchip electrophoretic method, a micro-liquid chromatography and the like.

BACKGROUND ART

Microchip electrophoresis employs a microchip having an electrophoretic flow path including a separation flow path formed inside a sheet-like member. A sample such as DNA, RNA or protein introduced into one end of a separation flow path is electrophoresed in a direction toward the other end of the separation flow path for separation by a voltage applied between both ends of the separation flow path, followed by detection.

In microchip electrophoresis, an apparatus has been developed that repeatedly uses a single microchip having a single electrophoretic flow path to thereby automatically perform filling of a buffer solution, injection of a sample, and detection of electrophoresed/separated sample components (see JP-A No. 10-246721).

In order to raise a throughput in analysis, electrophoretic apparatuses have also been proposed, each of which employs a microchip provided with multiple flow paths. An example of such apparatuses is one which employs a single microchip provided with twelve sample introduction flow paths and one separation flow path. In the example apparatus, after filling of a separation buffer solution into the flow paths, dispensation of samples are manually performed on all of the sample introduction flow paths, and thereafter electrophoresis is sequentially performed in the separation flow path to separate the samples into components thereof and to thereby obtain data (see Bunseki, No. 5, pp. 267 to 270 (2002)).

In another apparatus, a single cartridge is provided with twelve flow paths constituted of capillaries in which filling of a separation buffer solution, dispensation of samples, separation by electrophoresis and acquisition of data are performed automatically (Electrophoresis, 2003, 24, pp. 93 to 95).

In a micro-liquid chromatography, a microchip has been provided with a liquid flow path including a separation column, and a sample introduced into one end of the separation column is migrated in a direction toward the other end of the separation column to thereby separate the sample into components, followed by analyzing the components (see Anal. Chem., 70, p. 3790 (1998)).

For detection of a sample component separated in a main flow path, fluorescence detection is performed. In a fluorescence detector, a specific place of the main flow path is irradiated, or the main flow path is irradiated along a prescribed length thereof, with an excitation light to detect a fluorescence emitted due to excitation of the sample component. In that case, an excitation wavelength and a fluorescence wavelength to be detected are each limited to one kind.

The above apparatuses described in the journals "Bunseki" and "Electrophoresis" are useful in terms of throughput. However, both apparatuses in the examples are operated only under limitations that an operation is based on a batch processing and the same separation buffer solution is used on twelve samples, on all of which analysis has to be performed in the same condition. That is, it is impossible to employ a different separation buffer solution on each sample and to individually set conditions for electrophoresis on respective samples.

In a case where the number of samples is less than 12, one or more electrophoretic flow paths are wastefully not used, leading to cost increasing.

In the fluorescence detection, for example, there is a case where respective samples, prepared by making DNA subjected to fluorescence labeling with Cy3 (excitation wavelength of 550 nm/fluorescence wavelength of 570 nm) and with Cy5 (excitation wavelength of 650 nm/fluorescence wavelength of 668 nm), are intended to be simultaneously analyzed. However, since there has hitherto been only one kind of combination of the excitation wavelength and the fluorescence wavelength, simultaneous analysis of two or more fluorescence has not been possible. The same problem can be seen in liquid chromatography.

SUMMARY OF THE INVENTION

It is an object of the present invention to enable analysis conditions such as separation buffer solutions, electrophoretic conditions for electrophoresis, mobile phases or liquid feeding conditions for liquid chromatography, or fluorescence detection conditions to be set for each sample as well as to raise a separation throughput in electrophoresis or liquid chromatography.

The invention is directed to a analysis method in which a microchip provided with at least a main flow path performing migration of a sample solution for analysis inside a sheet-like member is employed, including a pretreatment step prior to the analysis step for the main flow path. The pretreatment steps are performed using a dispenser common to the multiple main flow paths and are performed such that when a pretreatment for one main flow path ends, a pretreatment for the next main flow path starts. Each of the analysis steps, subsequent to the pretreatment, is performed in a corresponding main flow path independently of the others, and the analysis steps are performed simultaneously to one another in the multiple main flow paths. In the analysis steps, a detection step is fluorescence detection performed by setting an excitation wavelength and a fluorescence wavelength in each of the main flow paths.

The term "analysis" includes, in its meaning, electrophoretic separation and detection in microchip eletrophoresis; separation, elution and detection in column in liquid chromatography; and reaction and detection of a reaction product in a reaction apparatus.

It is preferable that the main flow paths include a main flow path in which detection is performed by means of a plurality of excitation wavelengths and fluorescence wavelengths. In that case, one or more of independent excitation wavelengths and fluorescence wavelengths are combined so that analysis of each sample can be performed in the detecting portion.

With the combination independently selectable in the detector, it is also possible to select an analysis item consisting of the combination of the excitation wavelength and the fluorescence wavelength when requesting analysis.

An example of such a microchip analysis method is a microchip electrophoretic method. In its case, the microchip is provided with an electrophoretic flow path including a separation flow path as a main flow path, and the analysis step is a step of electrophoresing a sample introduced at one end of the separation flow path in the separation flow path in a direction toward the other end thereof due to a voltage applied between both ends of the separation path to thereby separate the sample into components thereof and to detect the components, while the pretreatment step includes at least filling of a separation buffer solution and injection of the sample into the electrophoretic flow path.

The electrophoresis step as the analysis step in the microchip electrophoretic method includes electrophoretic separation and detection. The electrophoretic separation includes zone electrophoresis and separation in the presence of a separation polymer or gel. Detection in a detecting portion is performed by the fluorescence measurement in which the separated sample component is irradiated with the excitation light to measure a fluorescence emitted due to the irradiation.

The pretreatment may include addition of a size marker, a fluorescent reagent or the like.

In a case where a different sample has been processed in advance in an electrophoretic flow path that is to then be filled with a separation buffer solution, the pretreatment step may include a step of cleaning the electrophoretic flow path with the separation buffer solution prior to filling of the separation buffer solution.

The electrophoretic flow path may be constituted of either only a separation flow path or a flow path of a cross-injection scheme in which a sample introducing flow path intersects with the separation flow path. In a case where the flow path is of the cross-injection scheme, the electrophoresis step includes a step of feeding a sample introduced at one end of the sample introducing flow path to an intersection of the sample introducing flow path and the separation flow path, and a step of separating the sample fed to the intersection in the separation flow path to detect components thereof.

Another example of such a microchip analysis method is of liquid chromatography. In its case, a microchip is provided with a liquid feed flow path including a separation column as a main flow path, and the analysis step is a liquid chromatography step of moving a sample introduced at one end of the separation column in a direction toward the other end thereof to thereby separate the sample into components thereof and to detect the components and the pretreatment step includes at least injection of the sample into the separation column.

The liquid chromatography step includes separation/elution and detection. The separation/elution includes separation and elution in an open tube column or a packed column, and the packed column also includes a nanostructure such as a pillar. Further, the elution includes a gradient elution in which a mobile phase is changed in composition with time.

As in the case of the microchip electrophoretic method, detection in liquid chromatography is also performed by the fluorescence measurement in which a separated sample component is irradiated with an excitation light to measure a fluorescence emitted due to the irradiation.

The invention is to repeatedly use a flow path formed in a microchip. The multiple flow paths in which processing is performed in the invention may be formed either in a single substrate or in multiple substrates in a separate state. Only one main flow path may be provided in a microchip because of ease in handling, in which case microchips in number equal to the number of main flow paths are arranged to perform processing.

A microchip processing apparatus of the invention is a processing apparatus for microchips each at least having a main flow path performing migration of a sample solution for analysis inside a sheet-like member, includes a holding part holding microchips so that the multiple main flow paths are provided; a pretreatment part common to the multiple main flow paths for performing a pretreatment step prior to an analysis step in each of the multiple main flow paths; a processing part for performing analysis in each of the main flow paths independently of the others, comprising a fluorescence detecting portion capable of selecting an excitation wavelength and a fluorescence wavelength independently in each of the main flow paths; and a control part controlling an operation in the pretreatment step so that when the pretreatment step in one main flow path ends, the process moves to a pretreatment step in the next main flow path and further controlling an operation in the processing part so that the analysis is subsequently performed in the main flow path where the pretreatment step has ended.

This microchip processing apparatus includes a microchip electrophoretic apparatus and a microchip liquid chromatograph.

In a case where the microchip processing apparatus is realized as a microchip electrophoretic apparatus, each of the microchips has an electrophoretic flow path including a separation flow path as a main flow path. In its case, the pretreatment part is a dispensation part performing at least filling of a separation buffer solution and injection of a sample into each of the electrophoretic flow paths, the processing part includes an electrophoresis high voltage power supply part capable of applying a migration voltage to each of the electrophoretic flow paths independently of the others and a fluorescence detection part detecting components of a sample separated in each electrophoretic flow path, and the control part controls an operation in the dispensation part so that when a pretreatment step in one electrophoretic flow path ends, the process proceeds to a pretreatment step in the next electrophoretic flow path and further controls an operation in the electrophoresis high voltage power supply part so that a migration voltage is applied across an electrophoretic flow path in which a pretreatment step has ended to thereby cause electrophoresis.

In a case where the microchip processing apparatus is realized as a microchip liquid chromatograph, each of the microchips is provided with a liquid feed flow path including a separation column as a main flow path and performs liquid chromatography in which an analysis proceeds in a way that a sample introduced at one end of each of the separation columns is moved in a direction toward the other end thereof to thereby separate the sample into components thereof and to detect the components. In its case, the pretreatment part is a dispensation part at least performing injection of the sample into each of the separation columns, the processing part includes a mobile phase feed mechanism capable of feeding a mobile phase into each of the separation columns independently of the others and the detection part detects components of the sample separated in each of the separation columns, and the control part controls an operation in the dispensation part so that when a pretreatment step in one separation column ends, the process proceeds to a pretreatment step in the next separation column and further controls an operation in the mobile phase feed mechanism so that a mobile phase is fed for separation in an separation column which a pretreatment step has ended.

In the above microchip liquid chromatograph, as in the case of the microchip electrophoretic method, detection in a detecting portion is performed by the fluorescence measurement in which the separated sample component is irradiated with the excitation light to measure a fluorescence emitted due to the irradiation.

Since, in a method of the invention, an analysis such as electrophoresis or a liquid chromatography can be performed in multiple flow paths simultaneously with each other, a throughput is raised as compared with serial processing in a way such that after a pretreatment and an analysis are performed in one flow path, a pretreatment and an analysis are performed in the next flow path.

In a case where the invention is applied to electrophoretic separation, since filling of a separation buffer solution is performed by a dispenser, a separation buffer solution suitable for a sample can be selected from a number of separation buffer solutions.

Since application of a migration voltage can be set at each of the electrophoretic flow paths independently of the others, conditions for electrophoresis separation can be set to each sample.

In a case where the invention is applied to liquid chromatography, an effect is obtained that a kind of an effluent, which is a mobile phase, and conditions for liquid feeding of the mobile phase can be selected for each sample.

Since the invention is not performed in batch processing, no waste occurs to any number of samples.

Further, since the combination of the excitation wavelength and the fluorescence wavelength can be independently selected for analysis of each sample, it is possible to simultaneously analyze a plurality of samples labeled by a plurality of fluorescence reagents. Namely, a multi-item analysis can be performed. In this manner, the processing line is not wasted regardless of the number of samples, to avoid relatively high running cost allowing reduction in processing time.

The foregoing and other objects, features, aspects and advantages of the present invention will become more apparent from the following detailed description of the present invention when taken in conjunction with the accompanying drawings.

DESCRIPTION OF THE PREFERRED EMBODIMENT

Figure 1:
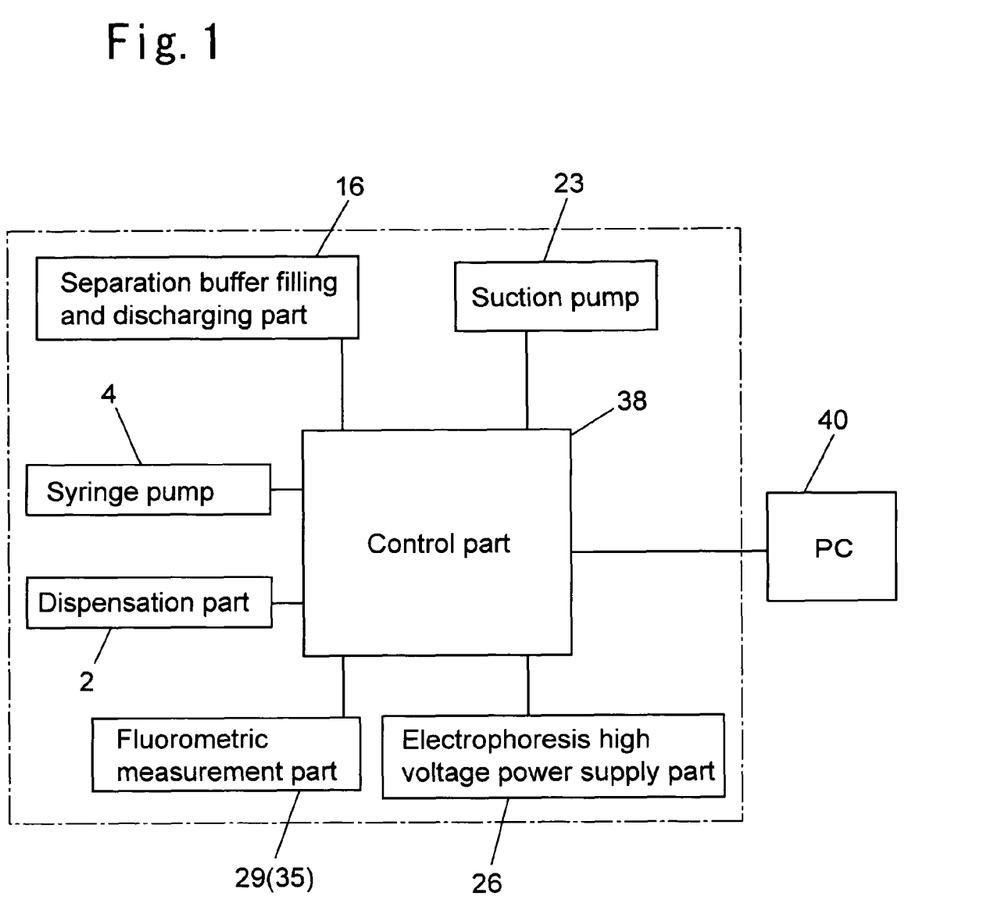
FIG. 1 is a block diagram schematically illustrating a part concerning a control part in an embodiment in which the invention is applied to a microchip electrophoretic apparatus.

FIG. 1 is a block diagram schematically illustrating a part concerning a control part in an embodiment in which the invention is applied to a microchip electrophoretic apparatus.

A dispenser 2 sucks a separation buffer solution and a sample separately to inject them into one end of an electrophoretic flow path in a microchip by a syringe pump 4, and the dispenser 2 is commonly provided to multiple electrophoretic flow paths. A separation buffer filling and discharging part 16 fills each of the eletrophoretic flow paths with a separation buffer solution injected into one end of the electrophoretic flow path by air pressure and discharges unnecessary separation buffer solution with a suction pump part 23. The part 16 is also commonly provided to the multiple electrophoretic flow paths in which processing is to be performed. A numerical symbol 26 denotes an electrophoretic high voltage power supply part applying a migration voltage to each of the electrophoretic flow paths independently of the others. A fluorometric measurement part 31 as an example of detection part detects components of a sample separated in each of the electrophoretic flow paths.

A control part 38 controls an operation in the dispenser 2 so that when filling of a separation buffer solution and injection of a sample into one electrophoretic flow path ends, the process proceeds to filling of a separation buffer solution and injection of a sample into the next electrophoretic flow path, further controls an operation in the electrophoretic high voltage power supply part 26 so that a migration voltage is applied to an electrophoretic flow path which injection of a sample has ended to thereby cause electrophoresis therein, and still further controls a detecting operation by the fluorometric measurement part 31.

A personal computer 40 as an external control apparatus commands an operation in the microchip electrophoretic apparatus and captures and processes data obtained by the fluorometric measurement part 31.

Figure 2:
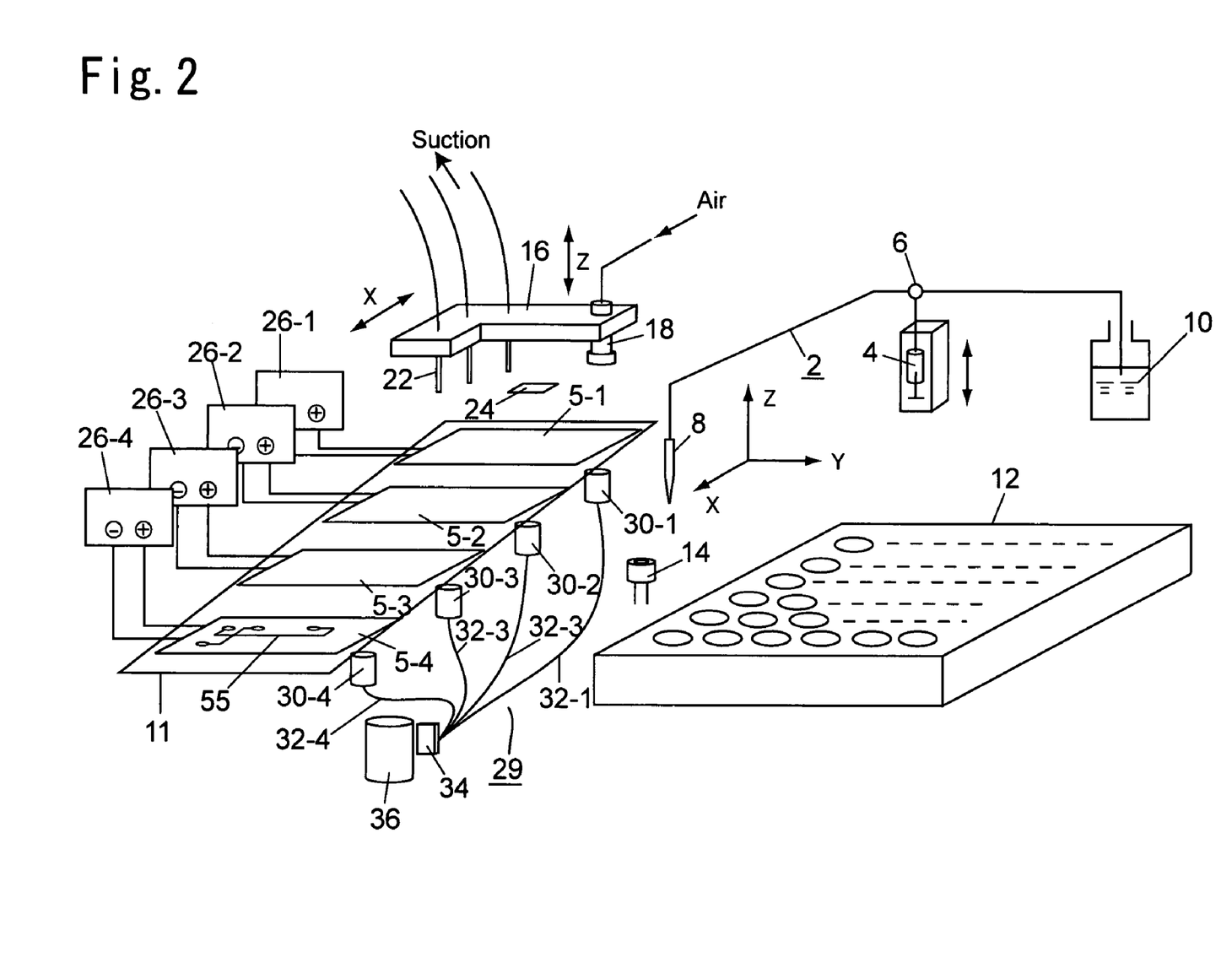
FIG. 2 is a perspective view schematically illustrating main parts of the embodiment

FIG. 2 schematically shows a main part of a microchip electrophoretic apparatus in one example in which each of microchips is capable of performing fluorescence detection by means of either of two kinds of fluorescence. Four microchips 5-1 to 5-4 are held on a holding part 11. Each of the microchips 5-1 to 5-4, as described later, has one electrophoretic flow path formed for processing one sample.

The dispenser 2 for dispensing separation buffer solutions and samples to the microchips 5-1 to 5-4 is provided with a syringe pump 4 performing suction and discharge, a probe 8 having a dispensing nozzle, and a container 10 for a cleaning liquid, wherein the probe 8 and the container 10 are connected to the syringe pump 4 by way of a three-way electromagnetic valve 6. The separation buffer solutions and the samples are contained in respective wells on a micro-titer plate 12, and the samples and the separation buffer solutions are dispensed to the microchips 5-1 to 5-4 by the dispenser 2. Note that the separation buffer solutions may be placed in the vicinity of the micro-titer plate 12 being contained in the respective containers. A cleaning part 14, which overflows with a cleaning liquid, cleans the probe 8.

The dispenser 2 is of a construction in which the three-way electromagnetic valve 6 is connected in a direction in which the probe 8 and the syringe pump 4 are connected to each other to suck a separation buffer solution or a sample from the probe 8 with the syringe pump 4 and to discharge the separation buffer solution and the sample into one of the electrophoretic flow paths in the microchips 5-1 to 5-4 with the syringe pump 4. When the probe 8 is cleaned, the three-way electromagnetic valve 6 is changed over in a direction in which the syringe pump 4 and the container 10 for a cleaning liquid are connected to each other, and the cleaning liquid is sucked into the syringe pump 4. Thereafter the probe 8 is dipped into the cleaning liquid of the cleaning part 14, and the three-way electromagnetic valve 6 is changed over to the side where the syringe pump 4 and the probe 8 are connected to each other to discharge the cleaning liquid from inside of the probe 8, thereby performing cleaning.

In order for the electrophretic flow path to be filled with a separation buffer solution dispensed into a reservoir at one end of the electrophoretic flow path of each of the microchips 5-1 to 5-4, a buffer filling and discharging unit 16 is commonly provided to the four microchips 5-1 to 5-4. An air discharge port 18 of the buffer filling and discharging unit 16 is pressed against the reservoir at the one end of the electrophoretic flow path of the one of the microchips 5-1 to 5-4 with airtightness and suction nozzles 22 are inserted into the other reservoirs of the electrophoretic flow path. Air is blown from the air discharge port 18 to push the separation buffer solution into the electrophoretic flow path while sucking the separation buffer solution which overflows from the other reservoirs with the nozzles 22 by a suction pump to discharge the overflowed solution to outside.

In order to apply a migration voltage to each of the electrophoretic flow paths of the microchips 5-1 to 5-4 independently of the others, an electrophoresis high voltage power supply 26 (26-1 to 26-4) is provided to each of the microchips 5-1 to 5-4 independently of the others.

The fluorometric measurement parts 29 detects components of a sample electrophoretically separated in the separation flow path 55 of a corresponding one of the microchips 5-1 to 5-4, have LEDs (light emitting diodes) 30-1 to 30-4 provided to the respective microchips for irradiating parts of the respective electrophoretic flow paths with excitation light, optical fibers 32-1 to 32-4 for receiving fluorescence emitted from the sample components which move in the electrophoretic flow paths and are excited by the excitation light from the LEDs 30-1 to 30-4, and an photomultiplier 36 receiving fluorescence through a filter 34 that removes an excitation light component from the fluorescence transmitted by the optical fibers 32-1 to 32-4 to transmit only fluorescence components. Each of the LEDs 30-1 to 30-4 is light-emitted while staggering light emitting thereof from the others, thereby enabling four kinds of fluorescence to be identified and detected with the one photomultifier 36. Note that an LD (laser diode) may be used as a light source for excitation light without being limited to an LED.

LEDs 30-1, 30-2 are LEDs that emit lights each including a wavelength light of 550 nm suitable for exciting a fluorescent dye Cy3, and a filter 34-1 to which fluorescence excited by the LEDs 30-1, 30-2 are led is an interference filter for transmitting a fluorescence of 570 nm therethrough. LEDs 30-3, 30-4 are LEDs that emit lights each including a wavelength light of 650 nm suitable for exciting a fluorescent dye Cy5. A filter 34-2 to which fluorescence excited by the LEDs 30-3, 3-04 are led is an interference filter for transmitting a fluorescence of 668 nm therethrough. A photo-multiplier 36 is capable of detecting both of the above fluorescence wavelengths.

In the case of this example, the fluorescence of 570 nm is detected in flow paths of microchips 5-1 to 5-2, and the fluorescence wavelength of 668 nm is detected in flow paths of microchips 5-3 to 5-4. Making the LEDs 30-1 to 30-4 emitted at staggered time allows identification and detection of four kinds of fluorescence in one photo-multiplier 36.

It is to be noted that the light source of the excitation light is not limited to the LED, and an LD (laser diode) may be employed.

Figure 3:
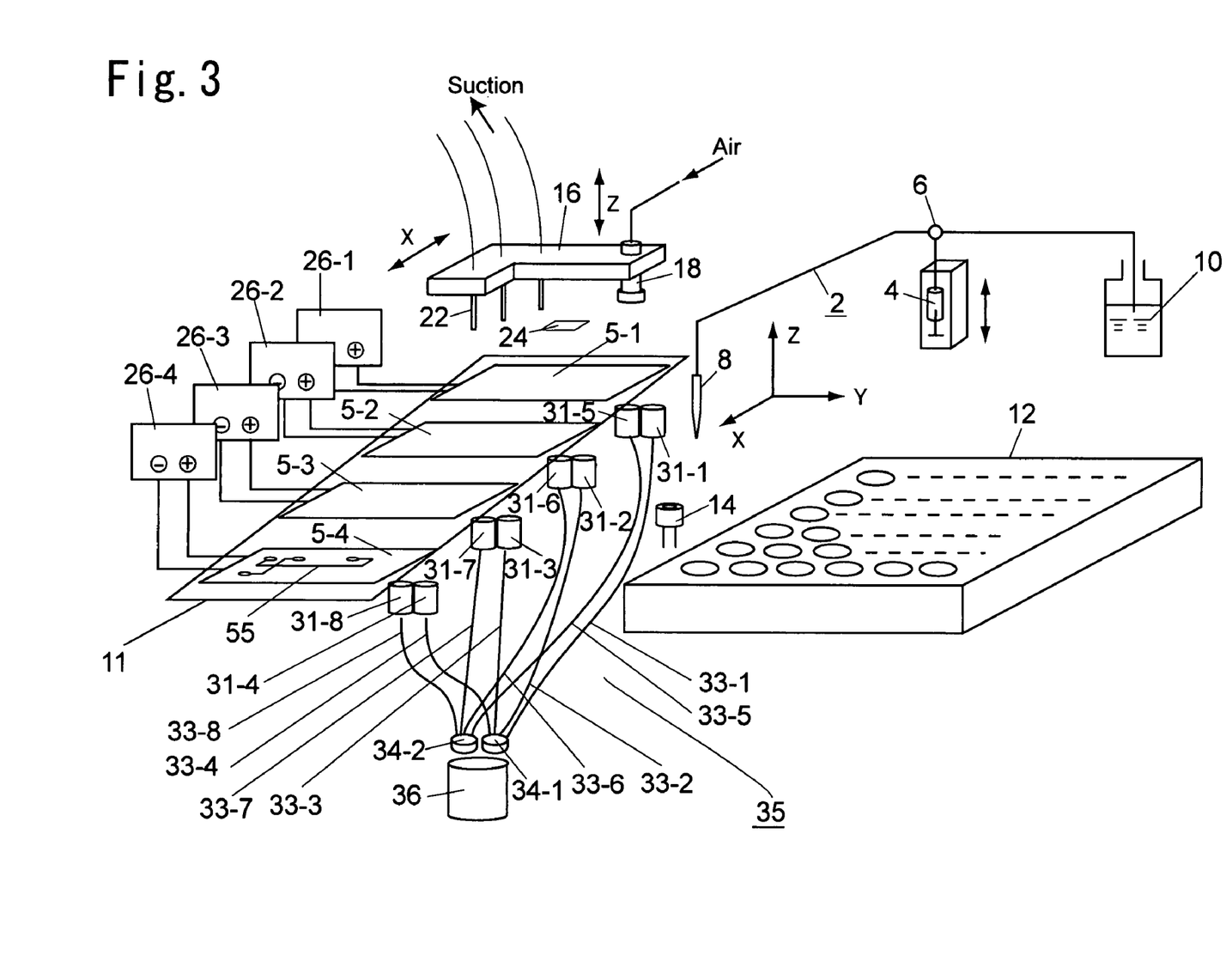
FIG. 3 is a perspective view schematically illustrating main parts of another embodiment

FIG. 3 schematically shows a main part of a microchip electrophoretic device in one example in which each of microchips is capable of performing fluorescence detection by means of two kinds of fluorescence. While each portion other than a fluorescence measurement portion is the same as in the example of FIG. 2, the device in this example is characterized in that different kinds of fluorescence wavelengths can be simultaneously measured since each microchip comprises a plurality of LEDs.

The fluorescence measurement portion 35 for detecting a sample component electrophoretically separated in a separation flow path 55 of each of the microchips 5-1 to 5-4 comprises: LEDs 31-1 to 31-8 which are respectively provided in the microchips 5-1 to 5-4 to irradiate part of the respective electrophoretic flow paths with excitation lights; optical fibers 33-1 to 33-8 for receiving fluorescence generated due to the excitation of the sample components moving along the electrophoretic flow paths by means of the excitation lights from the LEDs 31-1 to 31-8; filters 34-1, 34-2 for removing the excitation light components from the fluorescence from the optical fibers 33-1 to 33-8 to transmit only fluorescence components through the filters; and the photo-multiplier 36 for receiving the fluorescence through the filter 34-1 or 34-2.

The LEDs 31-1 to 31-4 are LEDs that emit lights each including a wavelength light of 550 nm suitable for exciting a fluorescent dye Cy3, and a filter 34-1 to which fluorescence excited by the LEDs 31-1 to 31-4 are led is an interference filter for transmitting a fluorescence of 570 nm therethrough. The LEDs 31-5 to 31-8 are LEDs that emit lights each including a wavelength light of 650 nm suitable for exciting a fluorescent dye Cy5, and a filter 34-2 to which fluorescence excited by the LEDs 31-5 to 31-8 are led is an interference filter for transmitting a fluorescence of 668 nm therethrough.

The respective light sources of the above optical systems are sequentially turned on and the two kinds of fluorescence are detected to scan a plurality of flow paths.

FIGS. 4A to 4C and FIG. 5 illustrate an example of a microchip of the embodiment A microchip in the invention means such an electrophoretic apparatus in which an electrophoretic flow path is formed in a substrate, wherein the apparatus is not necessarily limited to a small one in size.

Figure 4A:
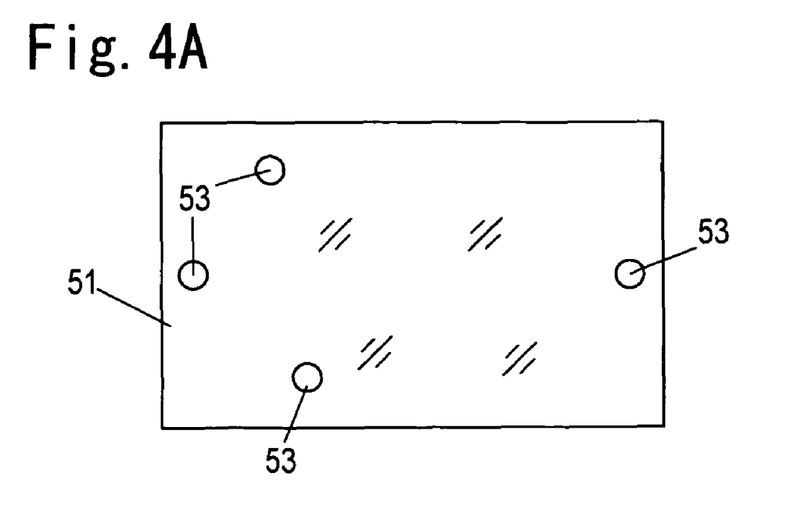
FIGS. 4(A) and 4(B) are plan views illustrating transparent sheet-like members constituting an example of a microchip and FIG. 4(C) is a front view of the microchip.
Figure 4B:
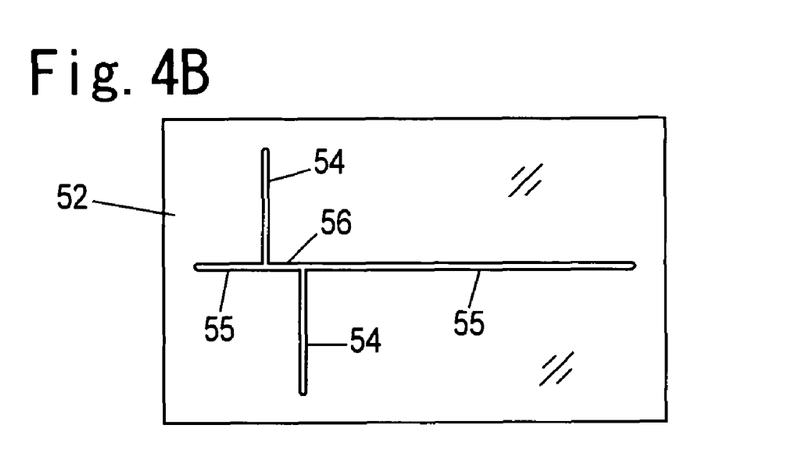
Figure 4C:
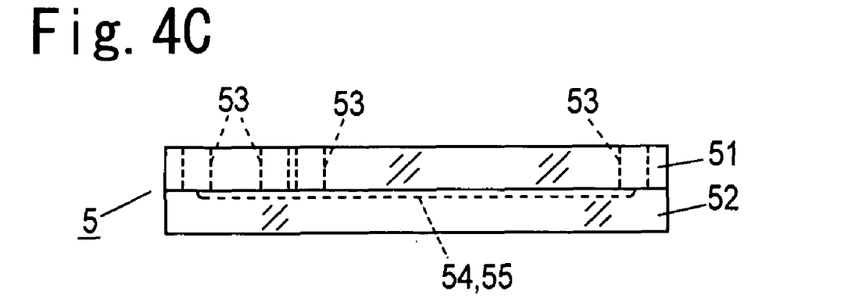

A microchip 5 is, as illustrated in FIGS. 4A to 4C, constituted of a pair of transparent substrates (substrates made of a quartz glass or other kinds of glass, or resin substrates) 51 and 52. Electrophoretic capillary grooves 54 and 55 intersecting with each other are, as illustrated in FIG. 4B, formed on a surface of one substrate 52, and reservoirs 53 are, as illustrated in FIG. 4C, formed as through holes at positions corresponding to ends of the grooves 54 and 55 in the other substrate 51. Both substrates 51 and 52 are, as illustrated in FIG. 4C, superimposed on one another and adhered to each other to form an electrophoretic separation flow path 55 and a sample introducing flow path 54 for introducing a sample into the separation flow path using the capillary grooves 54 and 55.

Figure 5:
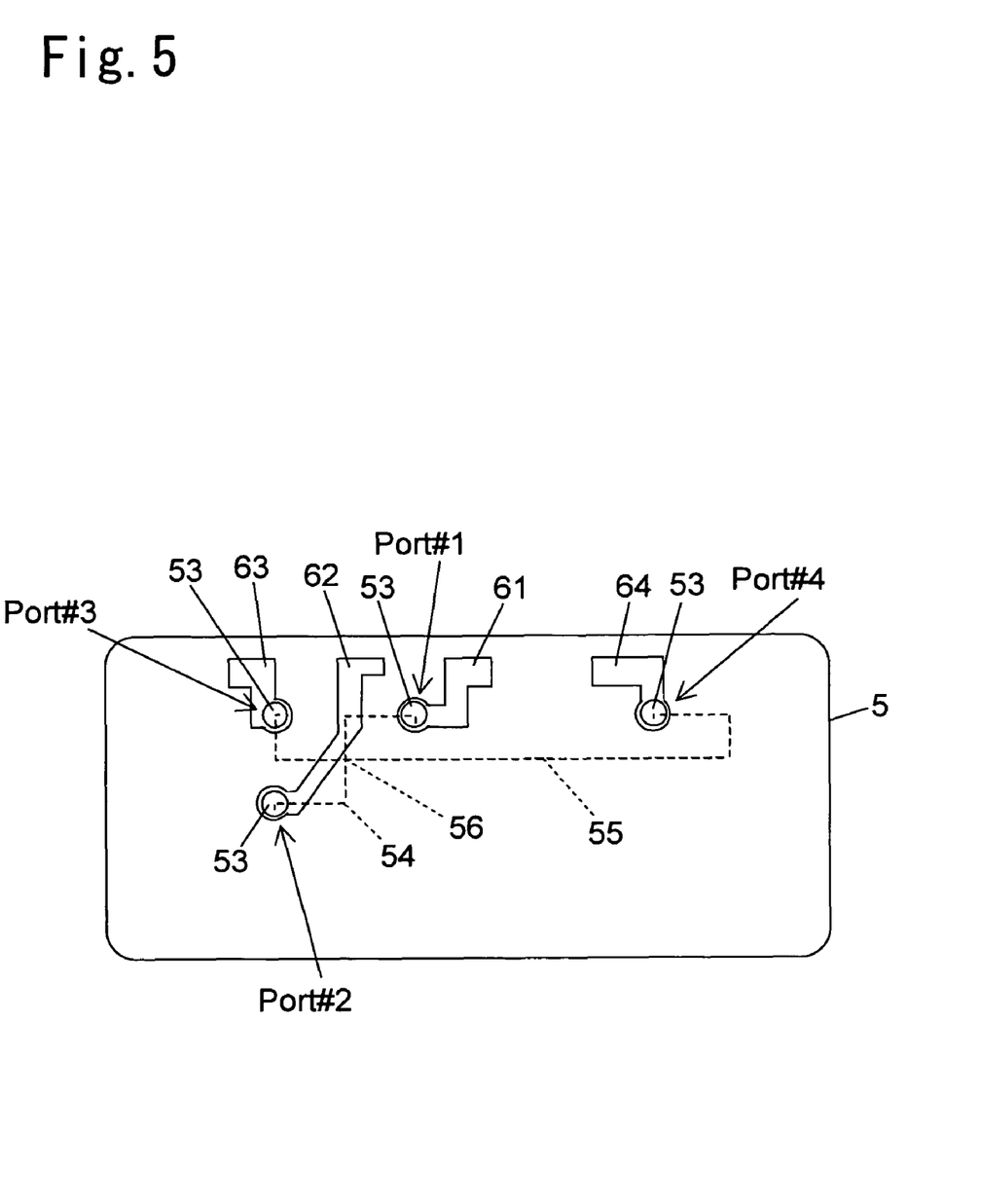
FIG. 5 is a plan view illustrating a microchip used in the embodiment

A microchip 5 is basically one illustrated in FIGS. 4A to 4C and for the sake of easy handling, as illustrated in FIG. 5, the microchip 5 on which electrode terminals for applying a voltage are formed in advance on the chip is employed. FIG. 5 illustrates a plan view of the microchip 5. The reservoirs 53 also work as ports to which a voltage is applied across the flow paths 54 and 55. Ports #1 and #2 are ports located at both respective ends of the sample introducing flow path 54 and ports #3 and #4 are ports located at both respective ends of the separation flow path 55. In order to apply a voltage to each port, electrode patterns with FIGS. 61 to 64 formed on the surface of microchip 5 are formed extending to the side ends of the microchip 5 from the ports, which are connected to the respective electrophoresis high voltage power supplies 26-1 to 26-4.

Figure 6:
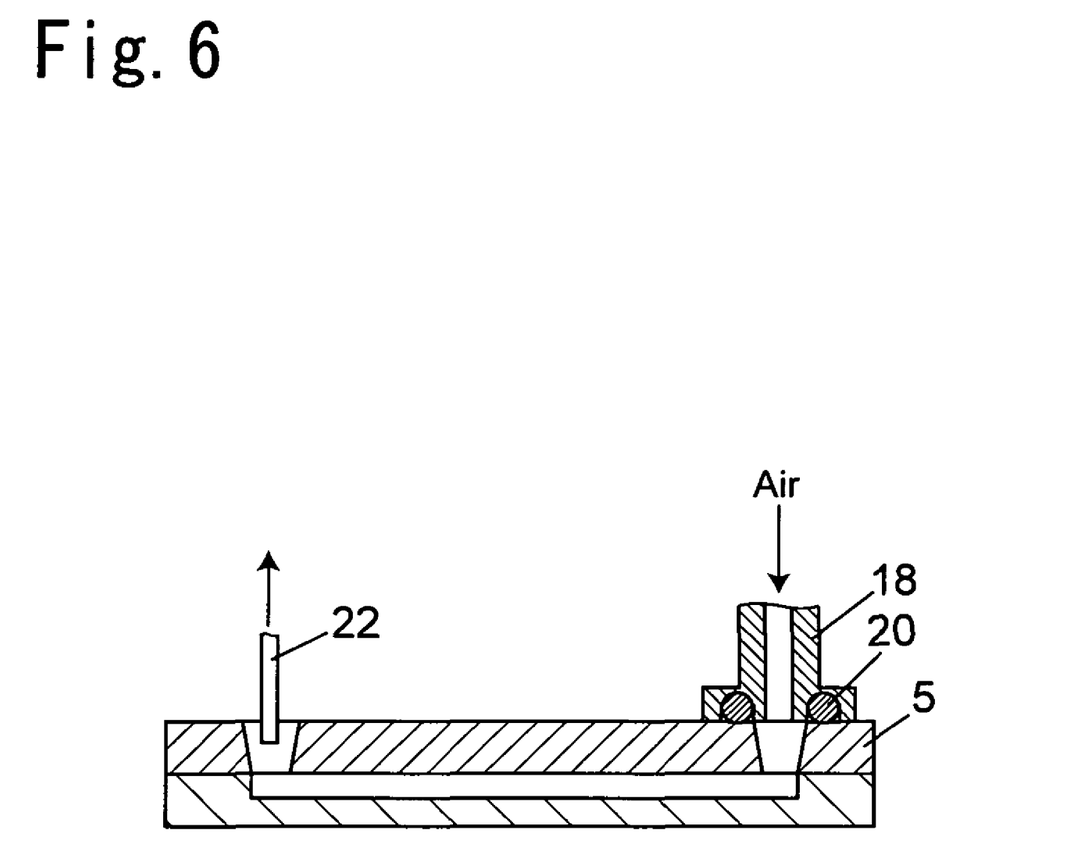
FIG. 6 is a sectional view schematically illustrating a state of connection between an air feed port in a buffer filling and discharging part and a microchip in the embodiment

FIG. 6 schematically illustrates a state of connection between an air feed port 18 in the buffer filling and discharging part 16 and the microchip 5. An O ring 20 is provided at the distal end of the air feed port 18 and the air feed port 18 is pressed against one reservoir of the microchip 5, and the air feed port 18 can thereby be mounted onto the electrophretic flow path of the microchip 5 with air-tightness, thereby enabling pressurized air to be fed into the flow path from the air feed port 18. The nozzles 22 are inserted to the other reservoirs and the unnecessary separation buffer solution overflowing flow paths is sucked and discharged.

Figure 7A:
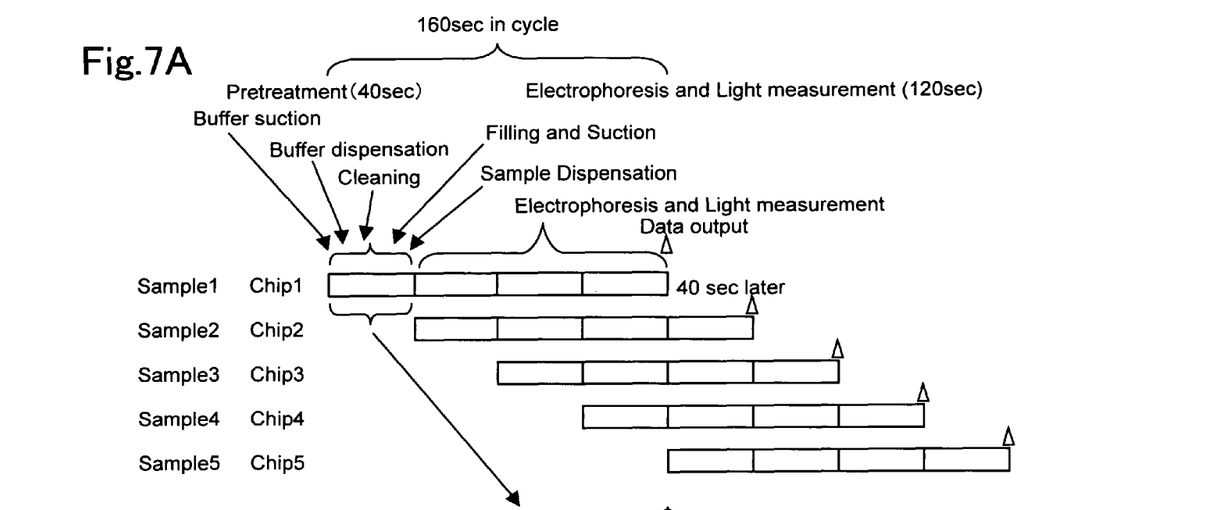
FIGS. 7(A) and 7(B) are time charts illustrating operations in the embodiment
Figure 7B:
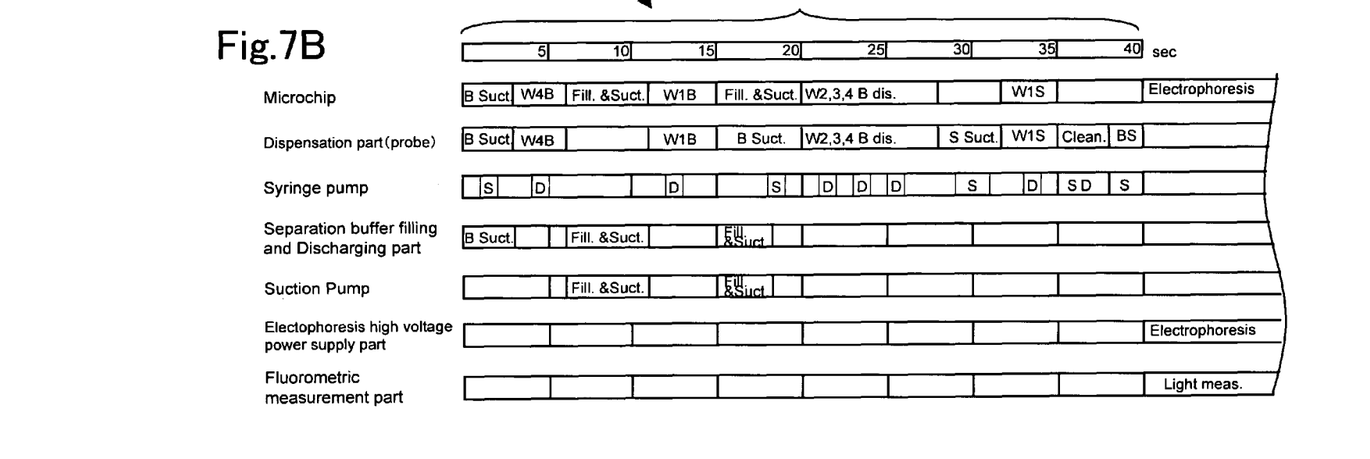

FIGS. 7A and 7B illustrate operations in an embodiment in a detailed manner. In the operations, a case is adopted where one electrophoretic flow path is formed on one microchip. Therefore, that the process proceeds from one microchip to the next microchip is the same in meaning as that the process proceeds from one electrophoretic flow path to the next eletrophoretic flow path.

FIG. 7A illustrates operations in the embodiment in which the pretreatment step and an electrophoresis and light measurement step are sequentially performed on four microchips while operating partly simultaneously with each other.

The steps are set in time; 40 sec are spent in the pretreatment step and 120 sec are spent in the electrophoresis and light measurement step. One cycle per microchip is 160 sec.

When a pretreatment step on one microchip ends, the process proceeds to a pretreatment on the next microchip without waiting for completion of the electrophoresis and light measurement step on the former microchip. That is, when the pretreatment step on the first microchip ends, a pretreatment step on the second microchip starts while an electrophoresis and light measurement step starts on the first microchip. When the pretreatment step on the second microchip ends, a pretreatment step on the third microchip starts while an electrophoresis and light measurement step starts on the second microchip. In such a way, the pretreatment step is repeated on microchips on a one on one basis, while separately from operations concerning pretreatment steps, the electrophoresis and light measurement step sequentially starts on a microchip on which a pretreatment has ended, with the result that the electrophoresis and light measurement steps are performed on multiple microchips simultaneously to each other. When the pretreatment step has been performed on a fourth microchip, similar processing is repeated on the first microchip in the second use thereof since an analysis has been completed on the first microchip.

In the electrophoresis step, a voltage is applied in order to guide a sample up to an intersection of the sample introducing flow path and the separation flow path from the sample introducing flow path and subsequent to this, separation by electrophoresis due to application of a voltage in the separation flow path is performed. In company with this, irradiation with light from LED is performed at a detection position and fluorometric measurement starts.

The pretreatment step is illustrated in FIG. 7B in a detailed manner. Numerical values at the uppermost level indicate times in sec. A lateral space with a title of "Microchip" illustrates contents of processing on one microchip. A lateral space with a title of "Dispensation part" illustrates operations of suction and discharge of a separation buffer solution and a sample through the probe 8 performed by the syringe pump 4. A lateral space with a title of "Syringe pump" illustrates operations of the syringe pump 4.

A lateral space with a title of "Separation buffer filling and discharging part" illustrates filling operations pushing a separation buffer solution dispensed onto a microchip into a flow path and operations performed by a suction pump in a suction step sucking and discharging the overflowing separation buffer solution, and a lateral space with a title of "Suction pump" illustrates operations of the suction pump for the separation buffer filling and discharging part 16. Lateral spaces with a title of "Electrophoresis high voltage power supply part" and with a title of "Fluorometric measurement part" illustrate operations of the respective parts.

In the lateral spaces, "B" means a buffer solution; "Suct" and "S" in the lateral space with the title of "Syringe pump" mean suction; "Fill. & Suct" means "filling and suction"; "W1 to W4" means the number of reservoirs; "D" and "dis" mean dispensation; and "S" in "W1S" means a sample.

In the lateral space with the title of "microchip", a first suction of separation buffer solution ("B suct") is a step of sucking and discharging a separation buffer solution having been used in the preceding analysis. In the next step ("W4B") step, a separation buffer solution is dispensed into a fourth reservoir. In the next step ("Fill. & Suct"), pressurized air is fed from the separation buffer filling and discharging part to push the separation buffer solution into a flow path while sucking and discharging the unnecessary separation buffer solution from the other reservoirs, thereby cleaning the flow path with the new separation buffer solution.

In order to clean a first reservoir in the next step ("W1B"), a separation buffer solution is newly dispensed into the first reservoir, and pressurized air is supplied to the fourth reservoir from the separation buffer filling and discharging part in the next step ("Fill. & Suct") to push the separation buffer solution of the fourth reservoir into the flow path to cause the flow path to be filled with the separation buffer solution while sucking and discharging the unnecessary separation buffer solution from the other reservoirs. Thereafter, the separation buffer solution is dispensed from second, third and fourth reservoirs in the next step ("W2, 3, 4 B dis.)". Thereby, filling of the separation buffer solution into the flow paths is completed.

Subsequently, a sample is sucked into the probe in the dispensation part for dispensing the sample and the sample is discharged into the first reservoir in a step ("W1S") for dispensation of the sample. The probe of the dispensation part is cleaned after dispensation of the sample and thereafter, the probe waits for suction of a separation buffer solution for the next sample. With all the steps performed, the pretreatment step for the flow paths in the microchip ends.

While in each of the microchips of the embodiment, a flow path of a cross injection scheme is adopted, no specific limitation is placed thereon and microchips each having a flow path constituted of only a separation flow path may be adopted.

While in the microchips of the embodiment, only one flow path is provided on one microchip, multiple flow paths may be formed on one microchip, in which case the invention has only to be applied to each flow path as a unit Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An analysis method in which microchips, each provided with at least a main flow path performing migration of a sample for analysis inside a sheet-like member is employed, comprising:
   pretreatment steps being performed using a dispenser common to the multiple main flow paths, and being performed such that when a pretreatment for one main flow path ends, a pretreatment for a next main flow path starts;
   analysis steps, each of which, subsequent to the pretreatment, being performed for a corresponding main flow path independently of the other main flow paths and simultaneously with a pretreatment step for the next main flow path, thereby the analysis steps being performed simultaneously with different start times to one another among the main flow paths; and
   a detection step in the analysis steps being fluorescence detection performed by setting a plurality of excitation wavelengths and a plurality of fluorescence wavelengths in each of the main flow paths,
wherein the main flow paths include a main flow path in which detection is performed by means of a plurality of excitation wavelengths and a plurality of fluorescence wavelengths, and
wherein the each of the microchips is associated with a respective plurality of light emitting devices and the plurality of fluorescence wavelengths are detected separately from each other and simultaneously through respective filters for transmitting respective fluorescence wavelengths for each sample component moving along the main flow path.

2. The analysis method according to claim 1, wherein an analysis item consisting of a combination of the excitation wavelength and the fluorescence wavelength is selected when requesting analysis.

3. The analysis method according to claim 1, wherein each of the microchips is provided with an electrophoretic flow path including a separation flow path as the main flow path,
each of the pretreatment steps includes at least filling of a separation buffer solution and injection of a sample into the electrophoretic flow path and
each of the analysis steps is an electrophoresis step and includes a separation step of electrophoresing the sample introduced at a first end of the separation flow path in a direction toward a second end thereof due to a voltage applied between both ends of the separation flow path to thereby separate the sample into components thereof; and a detection step detecting the separated components of the sample.

4. The analysis method according to claim 3, wherein in a case where a different sample has been analyzed in advance in the electrophoretic flow path that is to be then filled with a separation buffer solution, the pretreatment step includes a step of cleaning the electrophoretic flow path with the separation buffer solution prior to filling of the separation buffer solution.

5. The analysis method according to claim 3, wherein the electrophoretic flow path is a flow path of a cross-injection scheme in which a sample introducing flow path intersects with the separation flow path and
the electrophoresis step includes a step of feeding a sample introduced at one end of the sample introducing flow path to an intersection of the sample introducing flow path and the separation flow path and a step of separating the sample fed to the intersection in the separation flow path to detect components thereof.

6. The analysis method according to claim 1, wherein each of the microchips is provided with a liquid feed flow path including a separation column as on of the main flow paths,
each of the pretreatment steps includes at least injection of the sample into the separation column and
each of the analysis steps is a liquid chromatography step and includes a separation step of moving the sample introduced at a first end of the separation column in a direction toward a second end thereof to thereby separate the sample into components thereof; and a detection step of detecting the separated components of the sample.

7. The analysis method according to claim 1, wherein the multiple main flow paths are realized with the multiple microchips.

8. The analysis method according to claim 7, wherein each of the microchips is provided with only one main flow path and the multiple main flow paths are realized with the microchips in number equal to the number of the main flow paths.

9. An analysis apparatus for microchips, each at least having a main flow path performing migration of a sample for analysis inside a sheet-like member, comprising:
a holding part holding microchips so that the multiple main flow paths are provided;
a pretreatment part common to the multiple main flow paths for performing a pretreatment step prior to an analysis step in each of the multiple main flow paths;
a processing part for performing analysis in each of the main flow paths independently of the others, comprising a fluorescence detecting portion capable of selecting an excitation wavelength and a fluorescence wavelength independently in each of the main flow paths; and
a control part controlling an operation in the pretreatment part so that when a pretreatment step for one main flow path ends, a pretreatment for a next main flow path starts and further controlling an operation in the processing part so that an analysis is subsequently performed for the main flow path where the pretreatment step has ended,
wherein the fluorescence detecting portion is capable of measurement by means of a plurality of excitation wavelengths and a plurality of fluorescence wavelengths, wherein the fluorescence detecting portion has a plurality of filters transmitting respective fluorescence wavelengths for simultaneously detecting the plurality of fluorescence wavelengths separately from each other for each sample component moving along the main flow path.

10. The analysis apparatus according to claim 9, wherein each of the microchips has an electrophoretic flow path including a separation flow path as the main flow path,
the pretreatment part is a dispensation part performing at least filling of a separation buffer solution and injection of a sample into the electrophoretic flow path,
the processing part includes an electrophoresis high voltage power supply part capable of applying a migration voltage to the electrophoretic flow path independently of the others; and a detection part detecting components of the sample separated in the electrophoretic flow path, and
the control part controls an operation in the dispensation part so that when the pretreatment step for one electrophoretic flow path ends, the pretreatment step for the next electrophoretic flow path starts and further controls an operation in the electrophoresis high voltage power supply part so that the migration voltage is applied across the electrophoretic flow path which the pretreatment step has ended to thereby cause electrophoresis.

11. The analysis apparatus according to claim 9, wherein each of the microchips is provided with a liquid feed flow path including a separation column as the main flow path and performs liquid chromatography in which processing proceeds in a way such that the sample introduced at a first end of the separation column is moved in a direction toward a second end thereof to thereby separate the sample into components thereof and to detect the components,
the pretreatment part is a dispensation part at least performing injection of the sample into the separation column,
the processing part includes a mobile phase feed mechanism capable of feeding a mobile phase into the separation column independently of the others and the detection part detecting the components of the sample separated in the separation column and the control part controls an operation in the dispensation part so that when the pretreatment step for one separation column ends, the pretreatment step for the next separation column starts and further controls an operation in the mobile phase feed mechanism so that a mobile phase is fed for separation in the separation column which the pretreatment step has ended.

* * * * *